US006325990B1

(12) United States Patent
Laurent

(10) Patent No.: US 6,325,990 B1
(45) Date of Patent: Dec. 4, 2001

(54) FILM FORMING COMPOSITION FOR SPRAYING ON THE SKIN

(75) Inventor: Philippe Laurent, Oulins (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/051,719

(22) PCT Filed: Oct. 17, 1996

(86) PCT No.: PCT/FR96/01628

§ 371 Date: May 7, 1998

§ 102(e) Date: May 7, 1998

(87) PCT Pub. No.: WO97/15295

PCT Pub. Date: May 1, 1997

(30) Foreign Application Priority Data

Oct. 20, 1995 (FR) .................................................. 95 12393

(51) Int. Cl.[7] .................................................. A61K 9/12

(52) U.S. Cl. ............................ 424/45; 424/47; 424/70.1; 424/70.12; 424/DIG. 1; 424/DIG. 2; 514/63; 514/937

(58) Field of Search .............................. 424/45, 47, 70.1, 424/70.12, DIG. 1, DIG. 2; 514/937, 63

(56) References Cited

U.S. PATENT DOCUMENTS

| | | | | |
|---|---|---|---|---|
| 3,836,647 | | 9/1974 | Lange | 424/184 |
| 4,902,499 | * | 2/1990 | Bolich et al. | 424/70.1 |
| 5,658,557 | * | 8/1997 | Bolich et al. | 424/70.12 |

FOREIGN PATENT DOCUMENTS

| | | | |
|---|---|---|---|
| 205306 | * | 12/1986 | (EP) . |
| 0 478 456 | | 4/1992 | (EP) . |
| 0 679 392 | | 11/1995 | (EP) . |
| 95 30409 | | 11/1995 | (WO) . |

OTHER PUBLICATIONS

Patent Abstracts of Japan, vol. 13, No. 556 (C0664), Dec. 11, 1989, & JP 01 230514 A.

Patent Abstracts of Japan, vol. 13, No. 278 (C–611), Jun. 26, 1989, & JP 01 075416 A.

* cited by examiner

*Primary Examiner*—Raj Bawa
(74) *Attorney, Agent, or Firm*—Jacobson Holman, PLLC

(57) ABSTRACT

A composition is intended to form on the skin, by spraying from an erasol can, a film for the transdermal administration of an active agent, and the composition contains 0.01–10% by weight of lipophilic vitamins, hormones, nicotine, corticoids, retinoids, antimycosic agents, anistetics, anolgesics, or anti cancer agents for the skin, 0.5 to 25% by weight of an adhesive polysiloxane composition, 5 to 25% by weight of an absorption promoter, 25 to 95% by weight of a volatile solvent containing at least a volatile silicone, and 0.5 to 50% by weight of pressurized propellant gas, and the composition is substantially free from water.

14 Claims, No Drawings

FILM FORMING COMPOSITION FOR SPRAYING ON THE SKIN

The present invention relates to a novel composition for the transdermal administration of an active principle.

Transdermal systems which are applied to a limited area of the skin and which serve as a support or vehicle for one or more active principles, generally intended to exert a general action after release and passage across the skin barrier, were developed in the 1980s.

These systems, generally referred to as "transdermal patches", have a certain number of advantages over standard dermatological forms such as ointments, salves, gels, solutions and lotions:

direct and continuous passage into the general circulation, suppression of the first passage through the liver and/or of degradations in the digestive tract, with a consequent decrease in side effects, prolongation of the duration of action, maintenance of a constant level of active principles in the plasma, increasing the compliance with the prescription instructions by decreasing the administration frequency, decreasing the variations between individuals, controlling the dose administered by means of a membrane or matrix system with a reservoir, obtaining a constant concentration of active principle throughout the application.

Despite the degree of innovation provided by these systems, there are currently very few specialty medicines in this form. This is due to the fact that these devices require:

highly sophisticated manufacturing technology, rare production sites which belong to a few large groups which have a monopoly over them, this results in a high manufacturing cost and a high cost price and sale price. In summary, these systems are reserved for expensive products.

The present invention is directed towards providing novel compositions for the transdermal administration of an active principle which are very simple to use, and do not require heavy, complicated and expensive industrial plants, which are multi-purpose: as regards both the formulation and the modes of application during use, which are economically advantageous with a reduced production cost.

To this end, the subject of the present invention is a composition intended to form on the skin, by spraying from an aerosol can, a film for the transdermal administration of an active principle, this composition comprising:

a) a lipophilic active principle b) from 0.5 to 25% by weight, and advantageously from 5 to 25% by weight, of a silicone-based adhesive polymer composition c) from 0 to 25% by weight of an absorption promoter d) from 25 to 95% by weight of a volatile solvent comprising volatile silicones, and e) from 0.5 to 50% by weight of a pressurized propellent gas.

The subject of the present invention is also:

the use of a composition which comprises:

a) a lipophilic active principle b) from 0.5 to 25% by weight, and advantageously from 5 to 25% by weight, of a silicone-based adhesive polymer composition c) from 0 to 25% by weight of an absorption promoter d) from 25 to 95% by weight of a volatile solvent comprising volatile silicones, and e) from 0.5 to 50% by weight of a pressurized propellent gas, for producing on a patient's skin, by spraying from an aerosol can, a film for the transdermal administration of the active principle.

a process for the transdermal administration of an active principle to a patient, this process comprising the formation, on this patient's skin, of a film by spraying onto the skin, from an aerosol can, a composition which comprises:

a) a lipophilic active principle b) from 0.5 to 25% by weight, and advantageously from 5 to 25% by weight, of a silicone-based adhesive polymer composition c) from 0 to 25% by weight of an absorption promoter d) from 25 to 95% by weight of a volatile solvent comprising volatile silicones, and e) from 0.5 to 50% by weight of a pressurized propellent gas.

In the present invention, the term active principle mainly denotes a medicinal product or a substance having therapeutic properties.

These medicinal products are, in particular, lipophilic vitamins such as vitamins D and E and derivatives thereof, hormones such as calcitonin, steroids such as oestradiol and its esters and prednisone, nicotine, corticoids, retinoic derivatives, antimycosic agents such as ketoconazole, anaesthetics, analgesics such as lidocaine, or anticancer agents for the skin.

The percentages of the active principles in the compositions of the invention depend, needless to say, on the nature of the active principle. Generally, the percentages are from 0.01 to 10% by weight.

According to the invention, the expression silicone-based polymer composition is understood to refer to a composition containing both silicone-based polymers and silicone-based copolymers.

These silicones, which will be referred to according to the nomenclature in the CTFA (Cosmetic, Toiletry and Fragrance Association) dictionary, comprise in particular polydimethylsiloxane oils or polydimethylsiloxane oils modified with ionic or nonionic organic groups.

As examples of polydimethylsiloxane oils, mention will be made of dimethicones of formula:

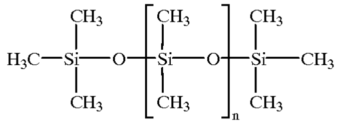

in which n is an integer less than 5000, and dimethiconols, which are dimethylsilicones with hydroxyl end groups.

As examples of modified polydimethylsiloxanes, mention will be made of dimethicone copolyols, which are dimethylsiloxane polymers containing polyoxyethylene and/or polyoxypropylene side chains.

The silicone-based adhesive polymer composition preferably represents 5 to 25% of the weight of the composition.

The absorption promoters can be chosen in particular from propylene glycol, hexylene glycol, propylene glycol dipelargonate, glyceryl monoethyl ether, diethylene glycol, monoglycerides, monooleate of ethoxylated glycerides (with 8 to 10 ethylene oxide units), azone (1-dodecylazacycloheptan-2-one), 2-(n-nonyl)-1,3-dioxolane, isopropyl myristate, octyl myristate, dodecyl myristate, myristyl alcohol, lauryl alcohol, lauric acid, lauryl lactate, terpineol, 1-menthol, D-limonene, β-cyclodextrin and its derivatives or surfactants such as polysorbates, sorbitan esters, sucrose esters, fatty acids and bile salts, or alternatively lipophilic and/or hydrophilic and/or amphiphilic products such as polyglycerol esters, N-methylpyrrolidone, polyglycosyl glycerides and cetyl lactate.

The absorption promoter preferably represents from 5 to 25% of the weight of the composition.

Volatile silicones or polysiloxanes and in particular polydimethylcyclosiloxanes (or cyclomethicone), i.e. compounds of formula:

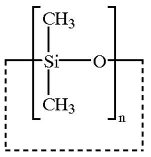

in which n is, on average, between 3 and 6, and in particular compounds in which n=4 or 5, as well as linear polysiloxanes such as hexamethyidisiloxane or dimethicones of low molecular mass, are used essentially as volatile solvent.

The volatile silicones preferably represent from 50 to 85% of the weight of the composition.

In addition, up to 25% and preferably up to 20% of other volatile solvents such as ethanol, isopropanol. chloroform, heptane or ethyl acetate, except for water, can also be used. It should in fact be noted that water is not compatible with the polysiloxanes used and should be avoided.

The propellent gas can be any propellent gas used to spray a liquid composition present in an aerosol can. This can be, in particular, a propellent gas of HFC type, such as HFC 134A ($CH_2F—CF_3$) which has been developed to replace CFCs, or alternatively relatively inert propellent gases such as nitrogen and carbon dioxide.

Cans fitted with a metering valve which allows determined amounts of pressurized composition to be sprayed will preferably be used. This makes it possible to deliver a determined amount of active principle onto the skin.

It is also possible to use a valve whose outlet is fitted with a cone which limits the dispersion of the spray. Films capable of releasing determined amounts of active principle in a uniform manner are thus formed on determined areas of the skin.

Examples of compositions according to the invention will be given below.

EXAMPLE 1

Composition Based on Retinoic Acid 50 mg of retinoic acid are dissolved in 20 g of isopropanol. A solution of 1 g of silicone consisting of a 13% solution of dimethiconol in volatile cyclomethicone, premixed with 60 g of volatile polydimethyl-cyclosiloxane, is added.

The solution obtained is introduced into aluminium aerosol cans in a proportion of 10 ml per can. The cans are closed by means of metering valves.

Lastly, the cans are filled with a propellant ($CH_2F—CF_3$) under pressure (about 5 to $7\times10^5$ Pa) in the can.

A composition is obtained which contains in each can, by weight:

| | |
|---|---|
| Retinoic acid | 0.05% |
| Isopropanol | 20% |
| Volatile silicone (polydimethylcyclosiloxane) | 60% |
| 13% Dimethiconol in cyclomethicone | 1% |
| $CH_2F$-$CF_3$ | 18.95% |

By pressing the metering valve, 100 microliters of this composition are sprayed onto the skin in the form of fine droplets which become deposited on the skin forming a film containing retinoic acid in a silicone matrix.

A dose of 100 microliters forms a film containing 50 micrograms of retinoic acid.

This film gradually releases the retinoic acid through the skin.

Such a composition can be used for treating acne.

EXAMPLE 2

Composition Based on Betamethasone

The process is performed as in Example 1, to prepare a composition containing:

| | |
|---|---|
| Betamethasone dipropionate (expressed as betamethasone | 0.05% |
| Propylene glycol | 10% |
| Volatile Silicone (polydimethylcyclosiloxane) | 60% |
| 13% Dimethiconol in cyclomethicone | 2% |
| $CH_2F$-$CF_3$ | 27.95%. |

A dose of 100 microliters forms a film containing 50 micrograms of betamethasone.

EXAMPLE 3

Composition Based on Lidocaine

The process is performed as in Example 1, to prepare a composition containing:

| | |
|---|---|
| Lidocaine | 5% |
| Ethylene glycol stearate | 10% |
| Ethanol | 10% |
| Volatile silicone (polydimethylcyclosiloxane) | 50% |
| 13% Dimethiconol in cyclomethicone | 2% |
| $CH_2F$-$CF_3$ | 23%. |

A dose of 100 microliters forms a film containing 5 mg of lidocaine.

EXAMPLE 4

Composition Based on Ketoconazole

The process is performed as in Example 1, to prepare a composition containing:

| | |
|---|---|
| Ketoconazole | 2% |
| Propylene glycol | 10% |
| Polysorbate 60 | 1% |
| Volatile silicone (polydimethylcyclosiloxane) | 60% |
| 13% Dimethiconol in cyclomethicone | 1% |
| $CH_2F$-$CF_3$ | 26%. |

A dose of 100 microliters forms a film containing 2 mg of ketoconazole.

What is claimed is:

1. Composition intended to form on the skin, by spraying from an aerosol can, a film for the transdermal administration of an active agent, the composition consisting essentially of:

a) 0.01–10% by weight of a lipophilic active agent selected from the group consisting of lipophilic vitamins, hormones, nicotine, corticoids, retinoids, antimycosic agents, anaesthetics, analgesics, and anticancer agents for the skin, b) 0.5 to 25% by weight of an adhesive polysiloxane composition, c) 5 to 25% by weight of an absorption promoter, d) 25 to 95% by weight of a volatile solvent containing at least a volatile silicone, and e) 0.5 to 50% by weight of a pressurized propellent gas, said composition being substantially free from water.

2. Composition according to claim 1, in which the adhesive polysiloxane composition is a polydimethylsiloxane oil or a polydimethylsiloxane oil modified with ionic or nonionic organic groups.

3. Composition according to claim 1, in which the volatile silicone is a polydimethylcyclosiloxane.

4. Composition according to claim 1, wherein said volatile silicone is present at an amount of 50 to 85% by weight.

5. Composition according to claim 1, wherein said volatile solvent contains ethanol, isopropanol, chloroform, heptane, or ethyl acetate present at an amount of 0 to 25% by weight.

6. Composition according to claim 1, wherein a volatile solvent other than said volatile silicone is present at an amount of 0 to 20% by weight.

7. Composition according to claim 1, which is present in an aerosol can fitted with a metering valve.

8. A method for transdermal administration of an active agent which comprises producing a film on a patient's skin, by spraying from an aerosol can, a film-forming composition consisting essentially of:

a) 0.01–10% by weight of a lipophilic active agent selected from the group consisting of lipophilic vitamins, hormones, nicotine, corticoids, retinoids, antimycosic agents, anaesthetics, analgesics, and anticancer agents for the skin, b) 0.5 to 25% by weight of an adhesive polysiloxane composition, c) 5 to 25% by weight of an absorption promoter, d) 25 to 95% by weight of a volatile solvent containing at least a volatile silicone, and e) 0.5 to 50% by weight of a pressurized propellent gas, said composition being substantially free of water.

9. Aerosol can intended to form on the skin, by spraying, a film for the transdermal administration of an active agent, this can containing a composition consisting essentially of:

a) 0.01–10% by weight of a lipophilic active agent selected from the group consisting of lipophilic vitamins, hormones, nicotine, corticoids, retinoic derivatives, antimycosic agents, anaesthetics, analgesics, and anticancer agents for the skin, b) 0.5 to 25% by weight of an adhesive polysiloxane composition, c) 5 to 25% by weight of an absorption promoter, d) 25 to 95% by weight of a volatile solvent containing at least a volatile silicone, and e) 0.5 to 50% by weight of a pressurized propellent gas, said composition being substantially free of water.

10. Process for the transdermal administration of an active agent to a patient, this process comprising the formation, on the patient's skin, of a film by spraying onto the skin, from an aerosol can, a composition consisting essentially of:

a) 0.01–10% by weight of a lipophilic active agent selected from the group consisting of lipophilic vitamins, hormones, nicotine, corticoids, retinoids, antimycosic agents, anaesthetics, analgesics, and anticancer agents for the skin, b) 0.5 to 25% by weight of an adhesive polysiloxane composition, c) 5 to 25% by weight of an absorption promoter, d) 25 to 95% by weight of a volatile solvent containing at least a volatile silicone, and e) 0.5 to 50% by weight of a pressurized propellent gas, said composition being substantially free of water.

11. Composition according to claim 1, wherein the adhesive polysiloxane composition is present at an amount of 5 to 25% by weight.

12. The method according to claim 8, wherein the adhesive polysiloxane composition is present at an amount of 5 to 25% by weight.

13. The aerosol can according to claim 9, wherein the adhesive polysiloxane composition is present at an amount of 5 to 25% by weight.

14. The process according to claim 10, wherein the adhesive polysiloxane composition is present at an amount of 5 to 25% by weight.

* * * * *